United States Patent
Crucs

(10) Patent No.: US 7,844,092 B2
(45) Date of Patent: *Nov. 30, 2010

(54) METHOD AND SYSTEM FOR AUTOMATIC INTRA-ORAL SENSOR LOCATING FOR IMAGE ACQUISITION

(75) Inventor: Kevin M. Crucs, Copley, OH (US)

(73) Assignee: Apteryx, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/549,683

(22) Filed: Aug. 28, 2009

(65) Prior Publication Data

US 2010/0007725 A1    Jan. 14, 2010

Related U.S. Application Data

(63) Continuation of application No. 11/459,444, filed on Jul. 24, 2006, now Pat. No. 7,599,538.

(51) Int. Cl.
*G06K 9/00* (2006.01)

(52) U.S. Cl. .............. 382/128; 382/293; 382/154; 382/130; 382/131; 382/132; 433/37; 433/43; 433/24; 433/45; 433/6; 378/38; 378/191; 378/98.8

(58) Field of Classification Search .......... 382/128, 382/133, 154, 294, 132; 345/419; 433/24, 433/29, 3.75, 213, 214; 702/152; 715/848–849, 715/815

See application file for complete search history.

(56) References Cited

U.S. PATENT DOCUMENTS

| | | | |
|---|---|---|---|
| 4,160,997 A | 7/1979 | Schwartz | |
| 5,434,418 A | 7/1995 | Schick | |
| 5,562,448 A | 10/1996 | Mushabac | |
| 5,995,583 A * | 11/1999 | Schick et al. | 378/38 |
| 6,134,298 A | 10/2000 | Schick et al. | |
| 6,592,371 B2 | 7/2003 | Durbin et al. | |
| 6,648,540 B2 | 11/2003 | Brisson et al. | |
| 6,652,141 B1 | 11/2003 | Cianciosi | |
| 7,068,825 B2 * | 6/2006 | Rubbert et al. | 382/128 |
| 7,286,954 B2 * | 10/2007 | Kopelman et al. | 702/152 |
| 7,361,020 B2 * | 4/2008 | Abolfathi et al. | 433/213 |
| 2002/0028418 A1 | 3/2002 | Farag et al. | |
| 2002/0094509 A1 | 7/2002 | Durbin et al. | |
| 2006/0154198 A1 * | 7/2006 | Durbin et al. | 433/29 |
| 2007/0036454 A1 | 2/2007 | Crucs | |

* cited by examiner

*Primary Examiner*—Wesley Tucker
*Assistant Examiner*—Nancy Bitar
(74) *Attorney, Agent, or Firm*—Hahn Loeser & Parks LLP

(57) ABSTRACT

A method and systems for capturing digital intra-oral images, while automatically determining a location of an intra-oral sensor placed within a mouth of a patient, is disclosed. A spatial frame-of-reference is established with respect to teeth within the mouth of the patient. An intra-oral digital imaging sensor is placed within the mouth of the patient adjacent to at least one tooth within the mouth that is to be imaged using the intra-oral sensor. Spatial location information is automatically generated such that the spatial location information defines how the intra-oral sensor is placed with respect to the spatial frame-of-reference. A digital image of at least one tooth is acquired using the intra-oral sensor and the spatial location information is automatically associated with the acquired digital image. The associated spatial location information may be used to automatically correlate the acquired image to a tooth or teeth within the mouth and/or to automatically orient the acquired image for display.

20 Claims, 7 Drawing Sheets

METHOD AND SYSTEM FOR AUTOMATIC INTRA-ORAL SENSOR LOCATING FOR IMAGE ACQUISITION

CROSS-REFERENCE TO RELATED APPLICATIONS/INCORPORATION BY REFERENCE

This U.S. patent application is a continuation of and claims priority to pending U.S. patent application Ser. No. 11/459,444 filed on Jul. 24, 2006 which is incorporated herein by reference in its entirety. U.S. patent application Ser. No. 11/078,810 filed on Mar. 11, 2005 is incorporated herein by reference in its entirety.

TECHNICAL FIELD

Certain embodiments of the present invention relate to digital imaging. More particularly, certain embodiments of the present invention relate to methods and systems for acquiring intra-oral digital images by automatically determining where in a patient's mouth an intra-oral digital imaging sensor has been placed.

BACKGROUND

Today, the process for capturing intra-oral digital images typically involves having to manually tell the system for which tooth or teeth an image is being captured. The system will typically prompt the user (e.g., a dentist or a technician) to tell the system which teeth are about to be imaged, based on where an intra-oral (IO) sensor has been placed in the mouth of a patient.

For example, an x-ray technician may place an intra-oral digital imaging sensor in the mouth of a patient and align an x-ray source. The technician then invokes x-ray capture using an x-ray image acquisition system. The technician is next prompted by the system for the teeth to be imaged. The technician may respond to the prompt by pressing keys or buttons, for example, on a user interface to indicate to the system which teeth are about to be imaged. Once the image is acquired, the technician may interact again with the user interface to display and orient the acquired image on a display and/or to store the image in a preferred format.

In order to take a next image of the patient, the technician is suppose to disinfect his/her hands before re-positioning the IO sensor within the mouth of the patient, since the technician touched the user interface. The process is repeated for acquiring a next image for as many images as are desired to be acquired (e.g., acquiring a full bite-wing series).

Having to manually interact with a user interface of the system between each image acquisition wastes time and calls into question whether the user is truly remaining sanitary for each acquisition (i.e., each time the user has to re-position the sensor in the patient's mouth). The user may forget to disinfect between, for example, two successive image acquisitions. Also, when the user positions the IO sensor in the mouth of the patient, the IO sensor may or may not be properly positioned to acquire an image of the desired tooth or teeth. For example, the user may think he/she is acquiring an image of teeth numbers 29-31 and manually tells the system such when, in reality, the IO sensor has been mis-positioned to acquire an image of teeth numbers 28-30.

Further limitations and disadvantages of conventional, traditional, and proposed approaches will become apparent to one of skill in the art, through comparison of such systems and methods with the present invention as set forth in the remainder of the present application with reference to the drawings.

SUMMARY

A first embodiment of the present invention provides a method of capturing intra-oral digital images. The method includes establishing a spatial frame-of-reference with respect to teeth within a mouth of a patient and placing an intra-oral digital imaging sensor within the mouth of the patient adjacent to at least one tooth within the mouth that is to be imaged by the intra-oral sensor. Additionally, the method includes automatically generating first spatial location information defining how the intra-oral sensor is placed with respect to the spatial frame-of-reference. The method further includes acquiring a first digital image of the at least one tooth using the intra-oral sensor and automatically associating the first spatial location information with the first digital image. The method also includes automatically associating the first digital image with one of a plurality of pre-defined areas in a tooth chart corresponding to the associated first spatial location information. The method further includes automatically orienting the first digital image to the one associated pre-defined area of the tooth chart in response to the first spatial location information or a default or pre-defined user preference of image orientation for the one associated pre-defined area of the tooth chart. The method also includes displaying the tooth chart and the oriented first digital image in the one associated area of the tooth chart. In accordance with various embodiments of the present invention, the intra-oral digital imaging sensor may include one of an x-ray imaging sensor, a thermal imaging sensor, and an ultrasonic imaging sensor. The first spatial location information may include relative position information and/or relative orientation information of the intra-oral sensor with respect to the spatial frame-of-reference. The spatial frame-of-reference may be established, at least in part, by arranging a plurality of directional sensors at known locations about a head of the patient. Each of the plurality of directional sensors is capable of interacting with the placed intra-oral sensor or holder to determine a directional vector between each directional sensor and the intra-oral sensor. The determined directional vectors are used to help generate the first spatial location information of the placed intra-oral sensor. The method may further include re-positioning the intra-oral digital imaging sensor within the mouth of the patient adjacent to at least one other tooth within the mouth that is to be imaged by the intra-oral sensor. The method may also include automatically generating second spatial location information defining how the intra-oral sensor is re-positioned with respect to the spatial frame-of-reference. The method may further include acquiring a second digital image of at least one other tooth with the intra-oral sensor, and automatically associating the second spatial location information with the second digital image. The method may also include automatically orienting the image on a display in response to the first spatial location information independent of any template or layout.

Another embodiment of the present invention comprises a system for capturing intra-oral digital images. The system includes means for establishing a spatial frame-of-reference with respect to teeth within a mouth of a patient, and an intra-oral digital imaging sensor to be placed within the mouth of the patient adjacent to at least one tooth within the mouth that is to be imaged by the intra-oral sensor. The system further includes means for automatically generating first spatial location information defining how the intra-oral sensor is placed with respect to the spatial frame-of-reference. The system also includes means for acquiring a first digital image of the at least one tooth with the intra-oral sensor and means for automatically associating the first spatial location information with the first digital image. The system also includes means for automatically associating the first digital image with one of a plurality of pre-defined areas in a tooth chart corresponding to the associated first spatial location information. The system also includes means for automatically orienting the first digital image to the one associated pre-defined area of the tooth chart in response to the first spatial location information or a default or pre-defined user preference of image orientation for the one associated pre-defined area of the tooth chart. The system also includes means for displaying the tooth chart and the oriented first digital image in the one associated area of the tooth chart. The means for establishing the spatial frame-of-reference may include a plurality of directional sensors arranged at known locations about a head of the patient. In accordance with various embodiments of the present invention, the intra-oral digital imaging sensor may include one of an x-ray imaging sensor, a thermal imaging sensor, and an ultrasonic imaging sensor. The means for automatically generating the first spatial location information may include a processor-based platform operationally connected to at least one of the means for establishing the spatial frame-of-reference, the intra-oral digital imaging sensor, the means for acquiring the first digital image, and the means for automatically associating the first spatial location information with the first digital image. The means for acquiring the first digital image may include a processor-based platform operationally connected to at least one of the intra-oral digital imaging sensor, the means for establishing a spatial frame-of-reference, the means for automatically generating the first spatial location information, and the means for automatically associating the first spatial location information with the first digital image. The means for automatically associating the first spatial location information with the first digital image may include a processor-based platform operationally connected to the means for automatically generating the first spatial location information and the means for acquiring the first digital image. The means for automatically generating the first spatial location information and the means for automatically associating the first spatial location information with the first digital image may include a processor-based platform operationally connected to the means for establishing the spatial frame-of-reference and the means for acquiring the first digital image. The means for automatically generating the first spatial location information, the means for acquiring the first digital image, and the means for automatically associating the first spatial location information with the first digital image may include a processor-based platform operationally connected to the means for establishing the spatial frame-of-reference and the intra-oral digital imaging sensor. The system may further include a display processing means operationally connected to the means for automatically associating the first spatial location information with the first digital image. The system may instead include a display processing means operationally connected to the means for automatically generating first spatial location information and the means for automatically associating the first spatial location information with the first digital image. The system may alternatively include a display processing means operationally connected to the means for acquiring the first digital image, the means for automatically generating first spatial location information, and the means for automatically associating the first spatial location information with the first digital image.

These and other advantages and novel features of the present invention, as well as details of an illustrated embodiment thereof, will be more fully understood from the following description and drawings.

DETAILED DESCRIPTION

Figure 1:
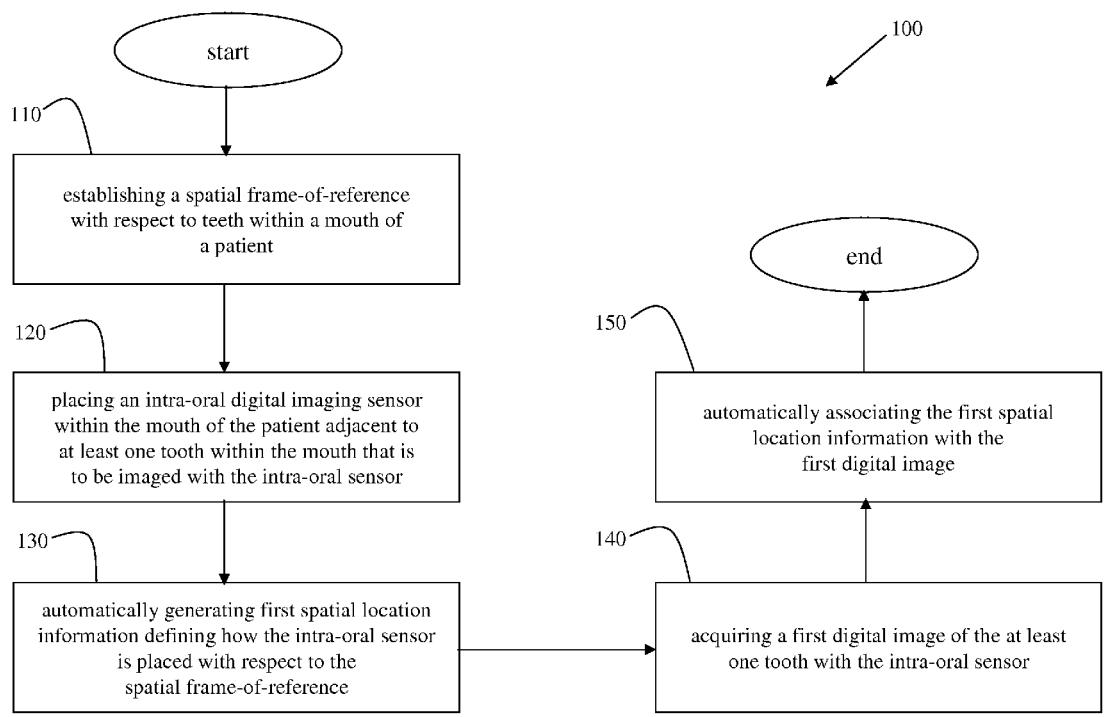
FIG. 1 is a flowchart of an embodiment of a method of capturing intra-oral digital images, in accordance with various aspects of the present invention.

FIG. 1 is a flowchart of an embodiment of a method 100 of capturing intra-oral digital images, in accordance with various aspects of the present invention. In step 110, a spatial frame-of-reference is established with respect to teeth within a mouth of a patient. In step 120, an intra-oral digital imaging sensor is placed within the mouth of the patient adjacent to at least one tooth within the mouth that is to be imaged using the intra-oral sensor. In step 130, first spatial location information is automatically generated, defining how the intra-oral sensor is placed in the mouth with respect to the spatial frame-of-reference. In step 140, a first digital image of the at least one tooth is acquired using the intra-oral sensor. In step 150, the first spatial location information is automatically associated with the first digital image.

Using the method 100 of FIG. 1, a dentist or technician does not have to manually interact with the image acquisition system to tell the system which teeth are being imaged. The established spatial frame-of-reference and the automatically generated spatial location information allow the placement of the IO sensor in the mouth to be automatically determined and associated with the correct acquired image.

Figure 2:
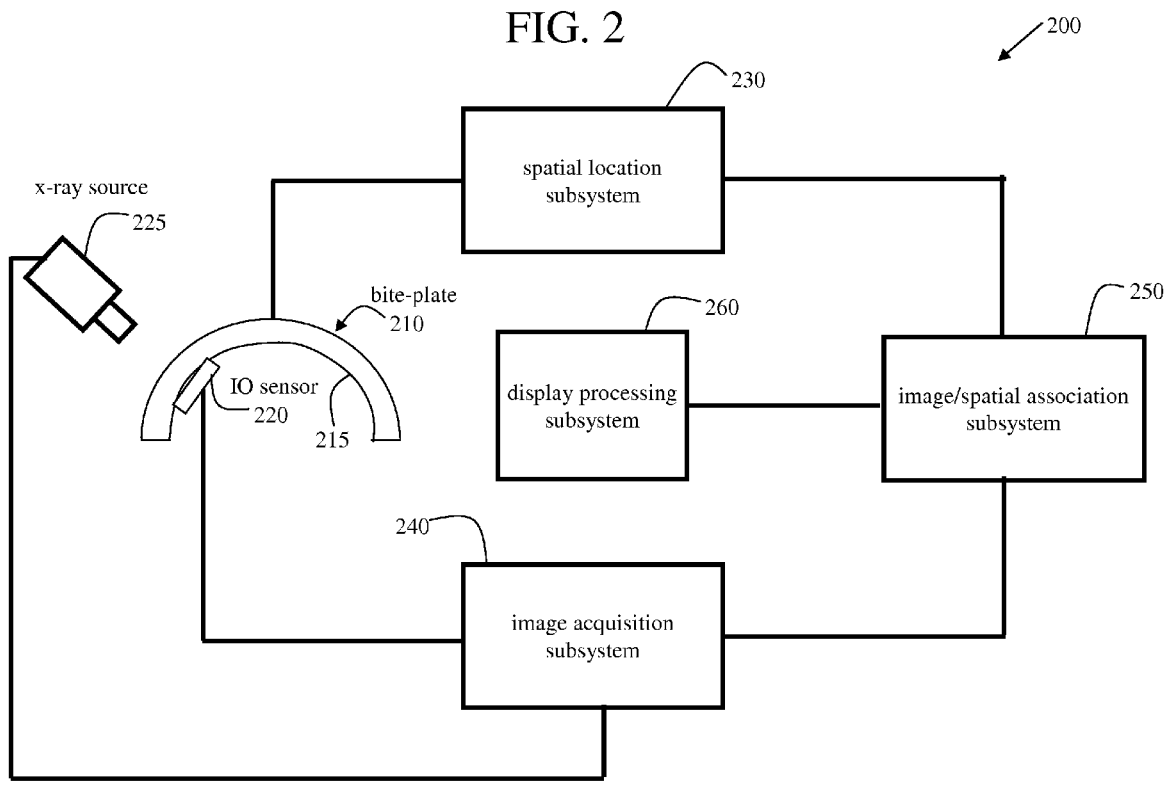
FIG. 2 is a schematic block diagram of an example first embodiment of a system for capturing intra-oral digital images using the method of FIG. 1, in accordance with various aspects of the present invention.

FIG. 2 is a schematic block diagram of an exemplary first embodiment of a system 200 for capturing intra-oral digital images using the method 100 of FIG. 1, in accordance with various aspects of the present invention. The system 200 includes a bite plate 210 serving as a means for establishing a spatial frame-of-reference with respect to teeth within the mouth of a patient. In accordance with an embodiment of the present invention, the bite plate 210 is placed within a mouth of the patient and the patient bites down on the bite plate 210 such that the bite-plate is aligned in a known manner with the teeth of the patient. Preferably, the bite plate 210 spans all of the teeth of the patient. However, certain bite plate configurations may only span a subset of teeth.

The system 200 also includes an intra-oral (IO) digital imaging sensor 220 which attaches to the bite plate 210. The IO sensor 220 may be an x-ray imaging sensor, a thermal imaging sensor, or an ultrasonic imaging sensor, in accordance with various embodiments of the present invention. If the IO sensor 220 is an x-ray imaging sensor, then an x-ray source 225 is provided. The IO sensor 220 may include a charge-coupled device (CCD) or any other type of filmless radiation sensor. Other types of IO sensors are possible as well in accordance with various alternative embodiments of the present invention. The bite plate 210 is made of materials that do not interfere with the particular type of IO imaging sensor 220. For example, if the IO sensor 220 is an x-ray imaging sensor, the bite plate 210 is constructed of materials that allow x-rays to pass through the bite plate 210, without degrading the resultant image, to any significant extent. The bite plate 210 has an inside or back surface 215.

Figure 3:
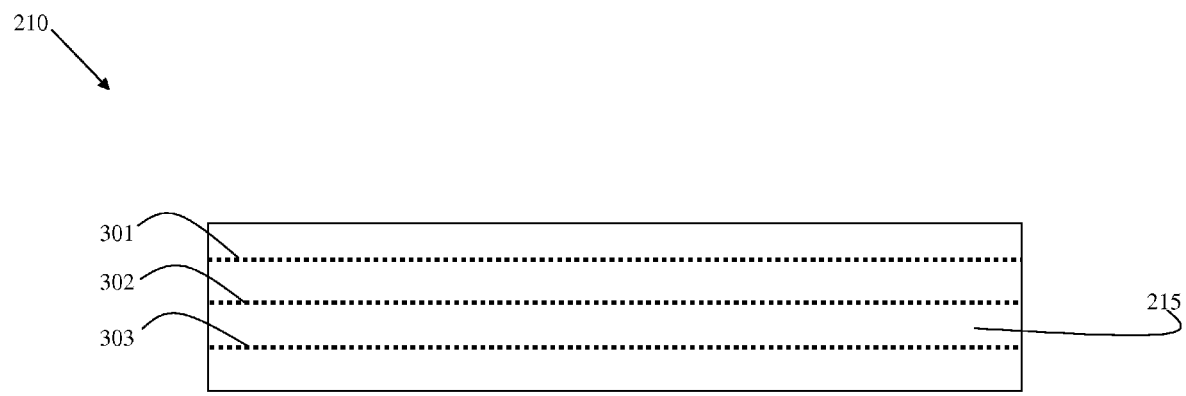
FIG. 3 is a schematic illustration of a rear view of an example embodiment of a bite plate, in accordance with various aspects of the present invention.

FIG. 3 is a schematic illustration of an inside or back surface 215 of an exemplary embodiment of the bite plate 210, in accordance with various aspects of the present invention. Even though the inside surface 215 of the bite plate 210 appears flat in FIG. 3, the inside surface 215 is actually curved to mimic the shape of a typical mouth as seen in FIG. 2. The bite plate 210 includes three attachment rows 301-303 spanning the inner back surface 215 of the bite plate 210. The IO sensor 220 is adapted to attach to any one of the rows 301-303 of the bite plate 210 at any one of a plurality of defined attachment points along the rows. As a result, the IO sensor 220 may attach anywhere along the top row 301, the middle row 302, or the bottom row 303 to allow imaging of certain teeth. Attachment to the top row 301 is accomplished in order to image a subset of the upper teeth and upper gums in the mouth of a patient. Attachment to the bottom row 303 is accomplished to image a subset of the lower teeth and lower gums in the mouth of the patient. Attachment to the middle row 303 is accomplished to image a subset of lower and upper teeth in the mouth of the patient. In accordance with alternative embodiments of the present invention, the bite plate may include fewer or more rows than that shown in FIG. 3.

Figure 4:
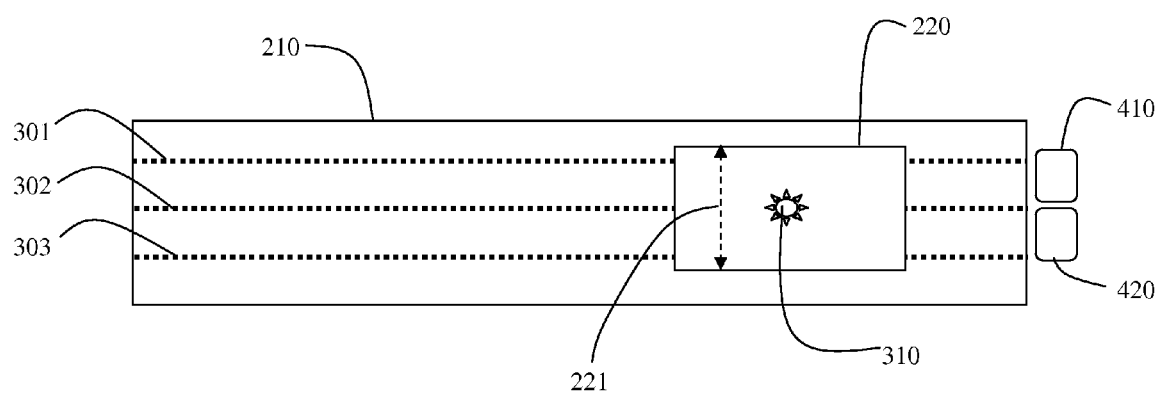
FIG. 4 is a schematic illustration of an IO sensor attached to the middle row of the bite plate of FIG. 3, in accordance with an embodiment of the present invention.

FIG. 4 is a schematic illustration of the IO sensor 220 attached to the middle row 302 of the bite plate 210, in accordance with an embodiment of the present invention. In accordance with an embodiment of the present invention, the IO sensor 220 is capable of attaching to the middle row 302 of the bite plate 210 and sliding along the middle row 302 such that the IO sensor 220 may be positioned along the surface 215 of the bite plate 210. As a result, a dentist or technician may place the IO sensor 220, at least approximately, with respect to the tooth or teeth that is/are desired to be imaged. In the example of FIG. 4, the single attachment point 310 is illustrated.

An illustration of two exemplary teeth 410 and 420 are shown to the right side of the bite plate 210 simply for reference. Tooth 410 is an exemplary upper tooth and tooth 420 is an exemplary lower tooth. As can be seen in FIG. 4, by positioning the IO sensor 220 in the middle row 302, a subset of both lower teeth and upper teeth may be imaged by the IO sensor 220.

In accordance with an embodiment of the present invention, each attachment row 301-303 of the bite plate 210 comprises a variable resistor such as a rheostat or a potentiometer. When the IO sensor 220 is attached to a point on one of the rows 301-303, a circuit is completed at that point such that a measured resistance value at the attachment point corresponds to a particular location along the row. As a result, the measured resistance value correlates to position on the bite plate 210. Referring again to FIG. 2, the resistance value is measured by a spatial location subsystem 230 which is operationally connected to the bite plate 210 to allow measurement of the resistance value. As an example, the resistance values, corresponding to the various attachment points on row 301, may range from 0 ohms at the left most attachment point to 500 ohms at the right most attachment point. Similarly, for row 302, the resistance values may range from 501 ohms to 1000 ohms. Also, for row 303, the resistance values may range from 1001 ohms to 1500 ohms.

As a result, no matter where on the bite plate 210 the IO sensor 220 is attached, the spatial location subsystem 230 will know the resistance value and, therefore, the corresponding attachment position on the bite plate 210. For a given type of IO sensor 210, the attachment positions on the bite plate 210 correlate to particular teeth within the mouth of the patient. The spatial location subsystem 230 is pre-programmed to perform the correlation. In accordance with an embodiment of the present invention, the spatial location subsystem 230 may be a simple processor-based platform running software and being capable of measuring the resistance value at the attachment point 310 and correlating the resistance value to a position in the mouth, thereby automatically generating spatial location information that defines the relative position in the mouth. As a result, the bite plate 210 serves as a means for establishing a spatial frame-of-reference with respect to the teeth within the mouth of the patient. In accordance with an embodiment of the present invention, the orientation of the bite plate 210 is always vertical (i.e., up and down) as shown by the double-ended arrow 221 of FIG. 4. Therefore, the IO sensor 220 may only be oriented one way (i.e., vertically) when attached to the bite plate 210.

Alternatively, the spatial location subsystem 230 may comprise an electronic circuit that generates spatial location information without using a processor.

Figure 5:
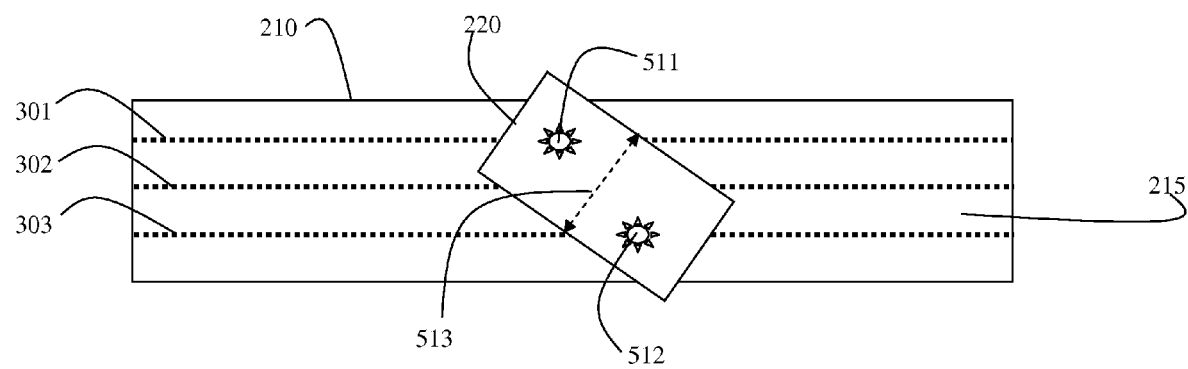
FIG. 5 is a schematic illustration of an IO sensor attached to the top row and the bottom row of the bite plate of FIG. 3, in accordance with another embodiment of the present invention.

In accordance with an alternative embodiment of the present invention, the IO sensor may be adapted to attach to the bite plate at two points as shown in FIG. 5. In FIG. 5, the IO sensor 220 attaches to the upper row 301 of the bite plate 210 at attachment point 511, and the IO sensor 220 attaches to the lower row 303 of the bite plate 210 at attachment point 512. The spatial location subsystem 230 of FIG. 2 is capable of measuring the resistance at both attachment points 511 and 512. By knowing the resistance values at the two attachment points 511 and 512, the spatial location subsystem can correlate the two resistance values to relative position within the mouth, and relative orientation as defined by the double-headed arrow 513, and generate the spatial location information. Such a diagonal orientation 513 may be desirable when trying to image a crooked tooth, or teeth in a region of the mouth that are ill-positioned in some manner.

Referring again to FIG. 2, the system 200 includes an image acquisition subsystem 240 operationally connected to the IO sensor 220 and serving as a means for acquiring digital images. The image acquisition subsystem 240 is also operationally connected to the x-ray source 225 when the IO sensor 220 is an x-ray imaging sensor. The image acquisition subsystem 240 comprises a processor-based platform running software and being capable of initiating image acquisition using the IO sensor 220 and storing the resultant image. Once the IO sensor 220 is attached to the bite plate 210 at a desired position in the mouth, a digital image may be acquired and stored in the image acquisition subsystem 240. The acquired digital image is typically stored digitally in memory in the image acquisition subsystem as a two-dimensional array of pixels, each pixel represented by a digital value.

In accordance with an embodiment of the present invention, the image acquisition subsystem includes an analog-to-digital (A/D) converter for converting analog signals from the IO sensor 220 to digital signals. Alternatively, the A/D converter may be separate and operationally connected between the IO sensor 220 and the image acquisition subsystem 240. The IO sensor 220 may be operationally connected to the image acquisition subsystem 240 either by wire or wirelessly, in accordance with various embodiments of the present invention.

The system 200 further includes an image/spatial association subsystem 250 serving as a means to automatically associate the first spatial location information (e.g., relative position and orientation information) generated by the spatial location subsystem 230 with the digital image acquired by the image acquisition subsystem 240. In accordance with an embodiment of the present invention, the image/spatial association subsystem 250 comprises a processor-based platform running software and being capable of receiving a stored digital image from the image acquisition subsystem 240 and spatial location information from the spatial location subsystem 230 and storing the digital image with the associated spatial location information. In accordance with an embodiment of the present invention, the spatial location information includes both position information and orientation information, defining both position of the IO sensor 220 in the mouth and orientation of the IO sensor 220 within the mouth at that determined position.

The system 200 also includes a display processing subsystem 260 operationally connected to the image/spatial association subsystem 250 for the purpose of receiving and processing the associated digital image and spatial location information for display. In accordance with an embodiment of the present invention, the display processing subsystem 250 automatically associates the digital image with one of a plurality of pre-defined areas in a tooth chart corresponding to the associated spatial location information. The display processing subsystem 250 automatically orients the digital image to the associated pre-defined area of the tooth chart in response to the spatial location information. In accordance with an alternative embodiment of the present invention, for example, a pre-defined user preference of image orientation for that pre-defined area of the tooth chart or a default image orientation is used to orient the image, especially if the spatial location information does not include orientation information. The display processing subsystem 260 then outputs a combined image of the tooth chart and the oriented digital image for display. In accordance with an embodiment of the present invention, the display processing subsystem 260 includes a display. Alternatively, the display processing subsystem 260 operationally interfaces to a separate display. U.S. patent application Ser. No. 11/078,810, filed on Mar. 11, 2005 and which is incorporated herein by reference, provides an exemplary description of how dental images may be arranged and displayed on a tooth chart template.

In accordance with an embodiment of the present invention, the user is able to position the IO sensor 220 anywhere in the mouth of the patient without worrying about filling in a predefined template or layout (e.g., independent of any template or layout). The user may, for example, want to skip sections of a template and may not want to take a whole series to fill in a predefined template but, instead, just certain parts of the series. Since the system 200 is able to automatically determine the position of the IO sensor 220 within the mouth of the patient, the user does not have to tell the system 200 to skip over image template locations. In fact, embodiments of the present invention do not have to be used with templates or layouts at all. The system 200 can be used to simply associate the positional location information with an image after it has been captured and to properly orient an image after it has been captured based on the associated information, whether multiple images are being successively captured or a single image is being captured.

In general, if the spatial position information includes orientation information, then this orientation information may be used to orient the acquired image for display. For example, if the system automatically determines that the sensor has been placed horizontally within the mouth, then the system will return and display a horizontally-oriented image. As another example, if the system automatically determines that the sensor has been placed vertically within the mouth, then the system will rotate the acquired image 90 degrees and display the rotated image, because that is how the sensor was placed in the mouth. However, a pre-defined user preference of orientation, or a default orientation, may be established ahead of time such that the preference or default is used to orient the acquired image for display (e.g., when only position information about the sensor is automatically available but orientation information is not).

Once a first digital image has been acquired and processed, a dentist or technician may re-position the intra-oral digital imaging sensor 220 within the mouth at a new attachment point (or points) on the bite plate 210. A second digital image and associated spatial location information may be obtained in a similar manner as previously described herein. This process may be repeated for as many images as the dentist or technician desires to capture, without the dentist or technician having to touch a user interface of the system with their hands or fingers.

Figure 6:
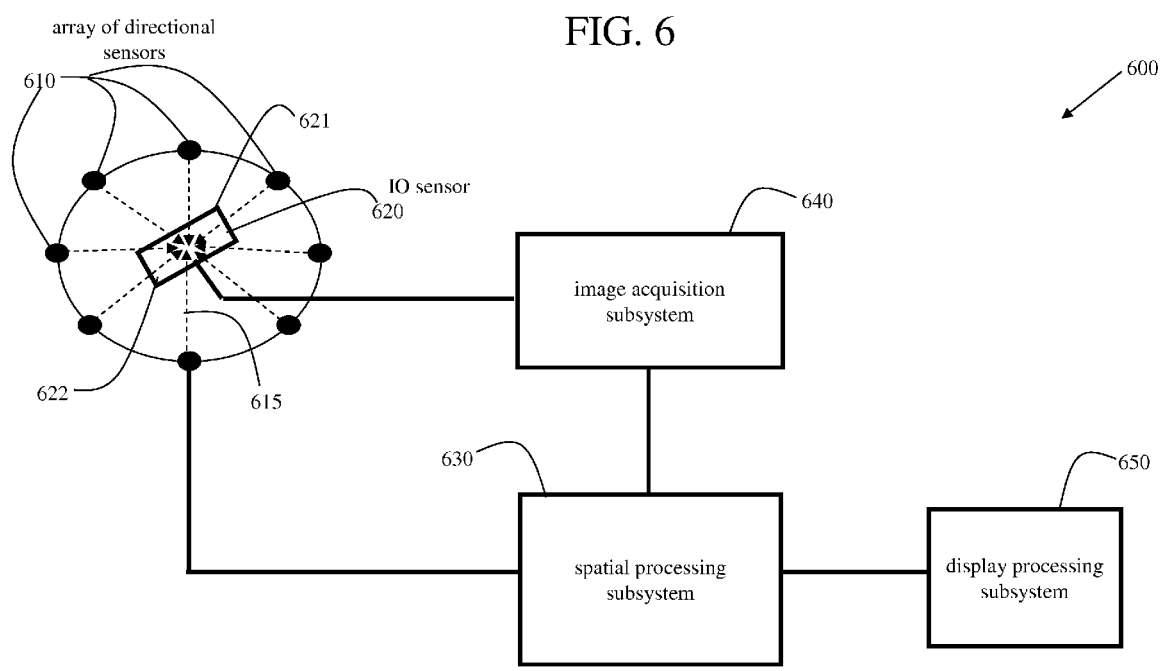
FIG. 6 is a schematic block diagram of an example second embodiment of a system for capturing intra-oral digital images using the method of FIG. 1, in accordance with various aspects of the present invention.

FIG. 6 is a schematic block diagram of an exemplary second embodiment of a system 600 for capturing intra-oral digital images using the method 100 of FIG. 1, in accordance with various aspects of the present invention. In FIG. 6, instead of a bite plate, an array of directional sensors 610 is used to determine the location of the IO sensor 620 within the mouth of the patient. In accordance with an embodiment of the present invention, the array of directional sensors 610 are arranged around a head of the patient with respect to the teeth of the patient to define a spatial (e.g., 3D volumetric) frame-of-reference. For example, the patient may wear a special helmet or configuration of straps containing the sensors 610. As another example, the array of sensors 610 may be mounted within a headpiece of a dental chair.

The array of directional sensors 610 may include active and/or passive RF sensors, magnetic sensors, or any other type of directional sensors that are capable of being used to determine a location (i.e., position and/or orientation) of an IO sensor 620 within a mouth of a patient. In accordance with certain embodiments of the present invention, the IO sensor 620 may include passive or active reflectors, receivers, or transmitters that interact with the array of directional sensors 610 to determine the location of the IO sensor 620 within the mouth.

In accordance with other embodiments of the present invention, the IO sensor may be placed in a sensor holder which is positioned within the mouth, where the sensor holder may include passive or active reflectors, receivers, or transmitters that interact with the array of directional sensors 610 to determine the location of the IO sensor 620 within the mouth. The IO sensor is capable of being placed within the sensor holder in only one way. As a result, the IO sensor 620 itself does not have to include such reflectors, receivers, or transmitters, and the IO sensor position is known with respect to the holder.

In accordance with an embodiment of the present invention, the signals from the array of directional sensors 610 include information defining a vector (e.g., vector 615) from each directional sensor to at least one point on the IO sensor 620 or holder. The spatial processing subsystem processes the vector information from each directional sensor and determines the location of the IO sensor 620 within the mouth of the patient (i.e., generates spatial location information), relative to the teeth of the patient.

For example, the IO sensor 620 (or holder) may include a small RF transmitter at one corner 621. The RF signal emitted by the RF transmitter is received by each directional sensor 610 such that an angular direction or vector in 3D space is determined between each directional sensor 610 and the RF transmitter of the IO sensor 620 (or holder). A second RF transmitter at an opposite corner 622 of the IO sensor 620 (or holder), and operating at a different RF frequency than the first RF transmitter, may be used with the first RF transmitter to allow determination of IO sensor orientation in the 3D volume as defined by the array of directional sensors 610.

Alternatively, the IO sensor 620 (or holder) may include two passive RF reflectors, one at a first corner 621 of the IO sensor 620 (or holder) and another at a second opposite corner 622 of the IO sensor 620 (or holder). The array of directional sensors 610 comprise transceivers that transmit RF signals which reflect off of the passive RF reflectors back to the transceivers. Each passive reflector may be tuned to reflect a different RF frequency. As a result, directional information is obtained between each directional sensor 610 and each passive RF reflector. Such directional information may be used to determine the spatial location (i.e., position and orientation) of the IO sensor 620 within the mouth of the patient.

Other technologies or combinations of technologies for the array of directional sensors 610 and the IO sensor 620 (or holder) may be used as well (e.g., magnets and magnetic sensors), in accordance with various alternative embodiments of the present invention, to provide directional information to a spatial processing subsystem 630.

The array of directional sensors 610 is operationally connected to a spatial processing subsystem 630. In the embodiment of FIG. 6, the spatial processing subsystem 630 is a combination of the spatial location subsystem 230 and the image/spatial association subsystem 250 of FIG. 2 and performs similar functions. For example, the spatial processing system 630 receives directional sensor information from the array of directional sensors 610 and automatically generates location information for the IO sensor 620.

The IO sensor 620 is operationally connected to an image acquisition subsystem 640. As described previously, the image acquisition subsystem 640 comprises a processor-based platform capable of initiating image acquisition using the IO sensor 620 and storing the resultant image. Once the IO sensor 620 is placed at a desired position in the mouth, a digital image may be acquired and stored in the image acquisition subsystem 640. The acquired digital image is typically stored digitally in memory in the image acquisition subsystem 640 as a two-dimensional array of pixels, each pixel represented by a digital value.

In addition to determining the spatial location of the IO sensor 620, the spatial processing subsystem 630 automatically associates the spatial location information (e.g., relative position and orientation information) with the digital image acquired by the image acquisition subsystem 640. In accordance with an embodiment of the present invention, the spatial processing subsystem 630 comprises a processor-based platform capable of receiving a stored digital image from the image acquisition subsystem 640 and associating and storing the digital image with the spatial location information. In accordance with an embodiment of the present invention, the spatial location information includes both position information and orientation information, defining both position of the IO sensor 620 in the mouth and orientation of the IO sensor 620 within the mouth at that determined position.

The system 600 also includes a display processing subsystem 650 operationally connected to the spatial processing subsystem 630 for the purpose of receiving and processing the associated digital image and spatial location information for display. In accordance with an embodiment of the present invention, the display processing subsystem 650 automatically associates the digital image with one of a plurality of pre-defined areas in a tooth chart corresponding to the associated spatial location information. The display processing subsystem 650 automatically orients the digital image to the associated pre-defined area of the tooth chart in response to the spatial location information and, for example, a pre-defined user preference of image orientation for that pre-defined area of the tooth chart, or a default image orientation. The display processing subsystem 650 then outputs a combined image of the tooth chart and the oriented digital image for display. In accordance with an embodiment of the present invention, the display processing subsystem 650 includes a display. Alternatively, the display processing subsystem 250 operationally interfaces to a separate display. Again, U.S. patent application Ser. No. 11/078,810, filed on Mar. 11, 2005 and which is incorporated herein by reference, provides an exemplary description of how dental images may be arranged and displayed on a tooth chart template. Again, tooth charts and/or templates or layouts may not be used at all, in accordance with certain embodiments of the present invention.

Once a first digital image has been acquired and processed, a dentist or technician may re-position the intra-oral digital imaging sensor 620 within the mouth at a new location. A second digital image and associated spatial location information may be obtained in a similar manner as previously described herein. This process may be repeated for as many images as the dentist or technician desire to capture.

Figure 7:
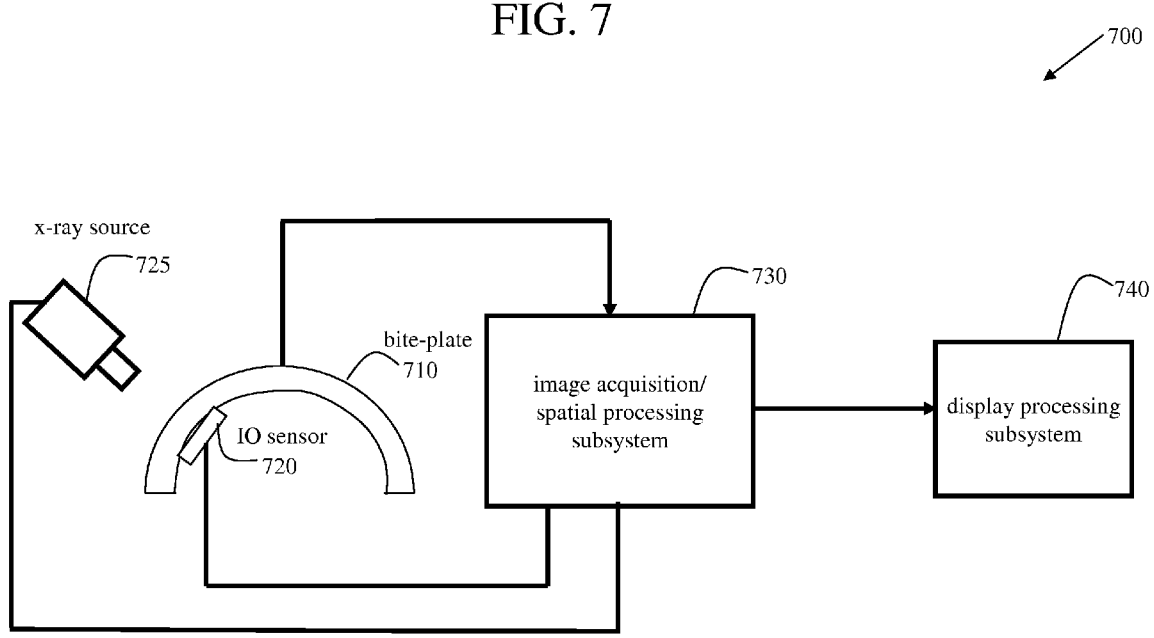
FIG. 7 is a schematic block diagram of an example third embodiment of a system for capturing intra-oral digital images using the method of FIG. 1, in accordance with various aspects of the present invention.

FIG. 7 is a schematic block diagram of an exemplary third embodiment of a system 700 for capturing intra-oral digital images using the method 100 of FIG. 1, in accordance with various aspects of the present invention. The system 700 is similar to the system 200 of FIG. 2 in that a bite plate 710 is used to establish a spatial frame-of-reference, similar to the bite plate 210. The system 700 includes an image acquisition/spatial processing subsystem 730 operationally connected to an IO sensor 720 and the bite plate 710 and serving as a means for acquiring digital images and generating spatial location information of the IO sensor 720. The image acquisition/spatial processing subsystem 730 combines the functions of the image acquisition subsystem 240, spatial location subsystem 230, and image/spatial association subsystem 250 into a single processor-based platform.

The image acquisition/spatial processing subsystem 730 is also operationally connected to an x-ray source 725 when the IO sensor 720 is an x-ray imaging sensor. The image acquisition/spatial processing subsystem 730 comprises a processor-based platform capable of initiating image acquisition using the IO sensor 720 and storing the resultant image. Once the IO sensor 720 is attached to the bite plate 710 at a desired position in the mouth, a digital image may be acquired and stored in the image acquisition/spatial processing subsystem 730. The acquired digital image is stored in memory in the image acquisition/spatial processing subsystem 730 as a two-dimensional array of pixels, each pixel represented by a digital value.

The image acquisition/spatial processing subsystem 730 also serves as a means to automatically associate the spatial location information (e.g., relative position and orientation information) with the acquired digital image. In accordance with an embodiment of the present invention, the spatial location information includes both position information and orientation information, defining both position of the IO sensor 720 in the mouth and orientation of the IO sensor 720 within the mouth at that determined position.

The system 700 also includes a display processing subsystem 740 operationally connected to the image acquisition/spatial processing subsystem 730 for the purpose of receiving and processing the associated digital image and spatial location information for display. In accordance with an embodiment of the present invention, the display processing subsystem 740 automatically associates the digital image with one of a plurality of pre-defined areas in a tooth chart corresponding to the associated spatial location information. The display processing subsystem 740 automatically orients the digital image to the associated pre-defined area of the tooth chart in response to the spatial location information. In accordance with an alternative embodiment of the present invention, for example, a pre-defined user preference of image orientation for that pre-defined area of the tooth chart or a default image orientation may be used to orient the image, especially when the spatial location information does not include orientation information. The display processing subsystem 740 then outputs a combined image of the tooth chart and the oriented digital image for display. Again, tooth charts and/or templates or layouts may not be used at all, in accordance with certain embodiments of the present invention.

In accordance with an embodiment of the present invention, the display processing subsystem 740 includes a display. Alternatively, the display processing subsystem 7400 operationally interfaces to a separate display.

Once a first digital image has been acquired and processed, a dentist or technician may re-position the intra-oral digital imaging sensor 720 within the mouth at a new attachment point (or points) on the bite plate 710. A second digital image and associated spatial location information may be obtained in a similar manner as previously described herein. This process may be repeated for as many images as the dentist or technician desire to capture.

In summary, embodiments of the present invention provide a method and systems for capturing intra-oral digital images while automatically determining the location (i.e., position and/or orientation) of an intra-oral digital imaging sensor placed within the mouth of a patient.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method of capturing intra-oral digital images, said method comprising:
   establishing an internal spatial frame-of-reference with respect to teeth within a mouth of a patient;
   placing an intra-oral digital imaging sensor within said mouth of said patient adjacent to at least one tooth within said mouth that is to be imaged using said intra-oral sensor, wherein said intra-oral sensor is not physically connected to said spatial frame of reference;
   automatically generating first spatial location information defining how said intra-oral sensor is placed with respect to said spatial frame-of-reference;
   acquiring a first digital image of said at least one tooth using said intra-oral sensor;
   automatically associating said first spatial location information with said first digital image;
   automatically associating said first digital image with one of a plurality of pre-defined areas in a tooth chart corresponding to said associated first spatial location information;
   automatically orienting said first digital image to said one associated pre-defined area of said tooth chart in response to said first spatial location information or a default or pre-defined user preference of image orientation for said one associated pre-defined area of said tooth chart; and
   displaying said tooth chart and said oriented first digital image in said one associated area of said tooth chart.

2. The method of claim 1 wherein said intra-oral digital imaging sensor comprises an x-ray imaging sensor.

3. The method of claim 1 wherein said intra-oral digital imaging sensor comprises a thermal imaging sensor.

4. The method of claim 1 wherein said intra-oral digital imaging sensor comprises an ultrasonic imaging sensor.

5. The method of claim 1 wherein said first spatial location information includes relative position information and/or relative orientation information of said intra-oral sensor with respect to said spatial frame of reference.

6. The method of claim 1 wherein said spatial frame-of-reference is established, at least in part, by arranging a plurality of directional sensors at known locations about a head of said patient.

7. The method of claim 6 wherein each of said plurality of directional sensors is capable of interacting with said placed intra-oral sensor or holder to determine a directional vector between each said directional sensor and said intra-oral sensor, and wherein said determined directional vectors are used to help generate said first spatial location information of said placed intra-oral sensor.

8. The method of claim 1 further comprising:
   re-positioning said intra-oral digital imaging sensor within said mouth of said patient adjacent to at least one other tooth within said mouth that is to be imaged by said intra-oral sensor;
   automatically generating second spatial location information defining how said intra-oral sensor is re-positioned with respect to said spatial frame-of-reference;
   acquiring a second digital image of said at least one other tooth with said intra-oral sensor; and
   automatically associating said second spatial location information with said second digital image.

9. The method of claim 1 further comprising automatically orienting said image on a display in response to said first spatial location information independent of any template or layout.

10. A system for capturing intra-oral digital images, said system comprising:
    means for establishing an internal spatial frame-of-reference with respect to teeth within a mouth of a patient;
    an intra-oral digital imaging sensor to be placed within said mouth of said patient adjacent to at least one tooth within said mouth that is to be imaged by said intra-oral sensor, wherein said intra-oral sensor does not physically connect to said spatial frame of reference;

means for automatically generating first spatial location information defining how said intra-oral sensor is placed with respect to said spatial frame-of-reference;

means for acquiring a first digital image of said at least one tooth with said intra-oral sensor;

means for automatically associating said first spatial location information with said first digital image;

means for automatically associating said first digital image with one of a plurality of pre-defined areas in a tooth chart corresponding to said associated first spatial location information;

means for automatically orienting said first digital image to said one associated pre-defined area of said tooth chart in response to said first spatial location information or a default or pre-defined user preference of image orientation for said one associated pre-defined area of said tooth chart; and means for displaying said tooth chart and said oriented first digital image in said one associated area of said tooth chart.

11. The system of claim 10 wherein said means for establishing said spatial frame-of-reference includes a plurality of directional sensors arranged at known locations about a head of said patient.

12. The system of claim 10 wherein said intra-oral digital imaging sensor comprises one of an x-ray imaging sensor, a thermal imaging sensor, and an ultrasonic imaging sensor.

13. The system of claim 10 wherein said means for automatically generating said first spatial location information includes a processor-based platform operationally connected to at least one of said means for establishing said spatial frame-of-reference, said intra-oral digital imaging sensor, said means for acquiring said first digital image, and said means for automatically associating said first spatial location information with said first digital image.

14. The system of claim 10 wherein said means for acquiring said first digital image includes a processor-based platform operationally connected to at least one of said intra-oral digital imaging sensor, said means for establishing said spatial frame-of-reference, said means for automatically generating said first spatial location information, and said means for automatically associating said first spatial location information with said first digital image.

15. The system of claim 10 wherein said means for automatically associating said first spatial location information with said first digital image includes a processor-based platform operationally connected to said means for automatically generating said first spatial location information and said means for acquiring said first digital image.

16. The system of claim 10 wherein said means for automatically generating said first spatial location information and said means for automatically associating said first spatial location information with said first digital image includes a processor-based platform operationally connected to said means for establishing said spatial frame-of-reference and said means for acquiring said first digital image.

17. The system of claim 10 wherein said means for automatically generating said first spatial location information, said means for acquiring said first digital image, and said means for automatically associating said first spatial location information with said first digital image includes a processor-based platform operationally connected to said means for establishing said spatial frame-of-reference and said intra-oral digital imaging sensor.

18. The system of claim 10 further comprising a display processing means operationally connected to said means for automatically associating said first spatial location information with said first digital image.

19. The system of claim 10 further comprising a display processing means operationally connected to said means for automatically generating first spatial location information and said means for automatically associating said first spatial location information with said first digital image.

20. The system of claim 10 further comprising a display processing means operationally connected to said means for acquiring said first digital image, said means for automatically generating first spatial location information, and said means for automatically associating said first spatial location information with said first digital image.

* * * * *